United States Patent
Quillin

(10) Patent No.: US 8,216,498 B2
(45) Date of Patent: Jul. 10, 2012

(54) CATHETER HAVING A COEXTRUDED FLUOROPOLYMER LAYER

(75) Inventor: Dan Quillin, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 442 days.

(21) Appl. No.: 12/207,692

(22) Filed: Sep. 10, 2008

(65) Prior Publication Data

US 2010/0063476 A1 Mar. 11, 2010

(51) Int. Cl.
| D01D 5/24 | (2006.01) |
| B29D 22/00 | (2006.01) |
| B32B 27/08 | (2006.01) |
| A61M 25/098 | (2006.01) |
| A61M 29/00 | (2006.01) |

(52) U.S. Cl. ............ 264/209.1; 428/35.9; 428/35.7; 428/36.91; 604/523; 604/524; 604/96.01; 604/95.01

(58) Field of Classification Search .......... 604/523, 604/96.01, 103, 524, 95.01; 264/209.1; 428/35.5, 428/413, 36.91, 35.9, 35.7
See application file for complete search history.

(56) References Cited

U.S. PATENT DOCUMENTS

| 3,561,493 A | 2/1971 | Maillard et al. |
| 3,618,614 A | 11/1971 | Flynn |
| 3,695,921 A | 10/1972 | Shepherd et al. |
| 3,814,137 A | 6/1974 | Martinez |
| 3,890,976 A | 6/1975 | Bazell et al. |
| 4,157,932 A | 6/1979 | Hirata |
| 4,171,416 A | 10/1979 | Motegi et al. |
| 4,211,741 A | 7/1980 | Ostoich |
| 4,265,848 A | 5/1981 | Rüsch |
| 4,282,876 A | 8/1981 | Flynn |
| 4,323,071 A | 4/1982 | Simpson et al. |
| 4,335,723 A | 6/1982 | Patel |
| 4,413,989 A | 11/1983 | Schjeldahl et al. |
| 4,596,563 A | 6/1986 | Pande |
| 4,597,755 A | 7/1986 | Samson et al. |
| 4,627,844 A | 12/1986 | Schmitt |
| 4,636,346 A | 1/1987 | Gold et al. |

(Continued)

FOREIGN PATENT DOCUMENTS

CA 2078201 A1 12/1992
(Continued)

OTHER PUBLICATIONS

Quantum—PLEXAR(r) Tie-Layer Resins "The Essential Bond for Coextruded Packaging," 8 sheets, dated before Sep. 24, 1997.

(Continued)

Primary Examiner — Kevin C Sirmons
Assistant Examiner — Bradley Thomas, Jr.
(74) Attorney, Agent, or Firm — Seager, Tufte & Wickhem LLC

(57) ABSTRACT

A catheter shaft including an elongate tubular member including a first polymeric layer and a second polymeric layer bonded to the first polymeric layer. The first polymeric layer is formed of a polymer generally not bondable to fluoropolymers, and the second polymeric layer is formed of a fluoropolymer bonded to the polymer of the first polymeric layer. The fluoropolymer of the second polymeric layer is a functionalized polyvinylidene fluoride which has a bonding affinity to the polymer of the first polymeric layer. The functionalized polyvinylidene fluoride includes reactive functional groups chemically bonded to a polymer chain of a polyvinylidene fluoride which readily bond to the polymer chain of the polymer of the first polymeric layer.

26 Claims, 4 Drawing Sheets

U.S. PATENT DOCUMENTS

| | | | |
|---|---|---|---|
| 4,646,719 A | 3/1987 | Neuman et al. | |
| 4,702,252 A | 10/1987 | Brooks et al. | |
| 4,707,389 A | 11/1987 | Ward | |
| 4,729,914 A | 3/1988 | Kliment et al. | |
| 4,744,366 A | 5/1988 | Jang | |
| 4,762,129 A | 8/1988 | Bonzel | |
| 4,763,654 A | 8/1988 | Jang | |
| 4,769,099 A | 9/1988 | Therriault et al. | |
| 4,775,371 A | 10/1988 | Mueller, Jr. | |
| 4,776,849 A | 10/1988 | Shinno et al. | |
| 4,782,834 A | 11/1988 | Maguire et al. | |
| 4,820,349 A | 4/1989 | Saab | |
| 4,863,449 A | 9/1989 | Therriault et al. | |
| 4,900,314 A | 2/1990 | Quackenbush | |
| 4,906,244 A | 3/1990 | Pinchuk et al. | |
| 4,921,483 A | 5/1990 | Wijay et al. | |
| 4,923,450 A | 5/1990 | Maeda et al. | |
| 4,940,179 A | 7/1990 | Soni | |
| 4,955,895 A | 9/1990 | Sugiyama et al. | |
| 4,960,410 A | 10/1990 | Pinchuk | |
| 4,976,690 A | 12/1990 | Solar et al. | |
| 4,976,720 A | 12/1990 | Machold et al. | |
| 4,981,478 A | 1/1991 | Evard et al. | |
| 4,994,018 A | 2/1991 | Saper | |
| 4,994,032 A | 2/1991 | Sugiyama et al. | |
| 4,994,047 A | 2/1991 | Walker et al. | |
| 5,006,119 A | 4/1991 | Acker et al. | |
| 5,026,377 A | 6/1991 | Burton et al. | |
| 5,035,694 A | 7/1991 | Kasprzyk et al. | |
| 5,041,089 A | 8/1991 | Mueller et al. | |
| 5,041,100 A | 8/1991 | Rowland et al. | |
| 5,047,045 A | 9/1991 | Arney et al. | |
| 5,059,269 A | 10/1991 | Hu et al. | |
| 5,063,018 A | 11/1991 | Fontirroche et al. | |
| 5,078,727 A | 1/1992 | Hannam et al. | |
| 5,085,649 A | 2/1992 | Flynn | |
| 5,100,381 A | 3/1992 | Burns | |
| 5,100,386 A | 3/1992 | Inoue | |
| 5,114,423 A | 5/1992 | Kasprzyk et al. | |
| 5,120,323 A | 6/1992 | Shockey et al. | |
| 5,147,315 A | 9/1992 | Weber | |
| 5,195,969 A | 3/1993 | Wang et al. | |
| 5,195,971 A | 3/1993 | Sirhan | |
| 5,221,270 A | 6/1993 | Parker | |
| 5,234,416 A | 8/1993 | Macaulay et al. | |
| 5,250,069 A | 10/1993 | Nobuyoshi et al. | |
| 5,254,090 A | 10/1993 | Lombardi et al. | |
| 5,267,959 A | 12/1993 | Forman | |
| 5,270,086 A | 12/1993 | Hamlin | |
| 5,272,012 A | 12/1993 | Opolski | |
| 5,279,560 A | 1/1994 | Morrill et al. | |
| 5,290,230 A | 3/1994 | Ainsworth et al. | |
| 5,290,306 A | 3/1994 | Trotta et al. | |
| 5,304,134 A | 4/1994 | Kraus et al. | |
| 5,318,032 A | 6/1994 | Lonsbury et al. | |
| 5,338,299 A | 8/1994 | Barlow | |
| 5,348,536 A | 9/1994 | Young et al. | |
| 5,356,709 A | 10/1994 | Woo et al. | |
| 5,383,853 A | 1/1995 | Jung et al. | |
| 5,397,306 A | 3/1995 | Nobuyoshi et al. | |
| 5,403,292 A | 4/1995 | Ju | |
| 5,405,338 A | 4/1995 | Kranys | |
| 5,409,495 A | 4/1995 | Osborn | |
| 5,423,754 A | 6/1995 | Cornelius et al. | |
| 5,425,712 A | 6/1995 | Goodin | |
| 5,439,454 A | 8/1995 | Lo et al. | |
| 5,460,608 A | 10/1995 | Lodin et al. | |
| 5,478,320 A | 12/1995 | Trotta | |
| 5,484,444 A | 1/1996 | Braunschweiler et al. | |
| 5,499,973 A | 3/1996 | Saab | |
| 5,501,759 A | 3/1996 | Forman | |
| 5,514,154 A | 5/1996 | Avellanet et al. | |
| 5,527,281 A | 6/1996 | Haas | |
| 5,533,985 A | 7/1996 | Wang | |
| 5,538,510 A | 7/1996 | Fontirroche et al. | |
| 5,545,151 A | 8/1996 | O'Connor et al. | |
| 5,549,552 A | 8/1996 | Peters et al. | |
| 5,558,737 A | 9/1996 | Brown et al. | |
| 5,562,127 A | 10/1996 | Fanselow et al. | |
| 5,571,089 A | 11/1996 | Crocker | |
| 5,620,649 A | 4/1997 | Trotta | |
| 5,643,209 A | 7/1997 | Fugoso et al. | |
| 5,653,691 A | 8/1997 | Rupp et al. | |
| 5,676,659 A | 10/1997 | McGurk | |
| 5,728,063 A | 3/1998 | Preissman et al. | |
| 5,728,088 A | 3/1998 | Magruder et al. | |
| 5,733,400 A | 3/1998 | Gore et al. | |
| 5,749,852 A | 5/1998 | Schwab et al. | |
| 5,792,814 A | 8/1998 | Oishi et al. | |
| 5,797,877 A | 8/1998 | Hamilton et al. | |
| 5,820,594 A | 10/1998 | Fontirroche et al. | |
| 5,824,173 A | 10/1998 | Fontirroche et al. | |
| 5,837,313 A | 11/1998 | Ding et al. | |
| 5,843,032 A | 12/1998 | Kastenhofer | |
| 5,853,400 A | 12/1998 | Samson | |
| 5,860,963 A | 1/1999 | Azam et al. | |
| 5,961,765 A | 10/1999 | Kastenhofer | |
| 6,027,477 A | 2/2000 | Kastenhofer | |
| 6,156,166 A * | 12/2000 | Koganezawa et al. | 204/266 |
| 6,165,166 A | 12/2000 | Samuelson et al. | |
| 6,319,228 B1 | 11/2001 | Kastenhofer | |
| 6,464,683 B1 | 10/2002 | Samuelson et al. | |
| 6,471,673 B1 | 10/2002 | Kastenhofer | |
| 6,509,098 B1 * | 1/2003 | Merrill et al. | 428/413 |
| 6,960,187 B2 | 11/2005 | Kastenhofer | |
| 2003/0118765 A1 | 6/2003 | Govaerts et al. | |
| 2006/0015064 A1 | 1/2006 | Kastenhofer | |
| 2007/0009565 A1 | 1/2007 | Pacetti et al. | |
| 2010/0022950 A1 * | 1/2010 | Anderson et al. | 604/100.01 |

FOREIGN PATENT DOCUMENTS

| | | |
|---|---|---|
| EP | 0 277 368 A1 | 8/1988 |
| EP | 0 279 959 B1 | 8/1988 |
| EP | 0 298 634 A1 | 1/1989 |
| EP | 0 351 687 A2 | 1/1990 |
| EP | 0 358 117 B1 | 3/1990 |
| EP | 0 380 102 A1 | 8/1990 |
| EP | 0 420 488 A1 | 4/1991 |
| EP | 0 436 501 B1 | 7/1991 |
| EP | 0 452 123 A1 | 10/1991 |
| EP | 0 456 342 A1 | 11/1991 |
| EP | 0 520 692 A1 | 12/1992 |
| EP | 0 530 201 B1 | 3/1993 |
| EP | 0 650 740 A1 | 5/1995 |
| EP | 0 669 142 A2 | 8/1995 |
| EP | 0 803 264 A1 | 10/1997 |
| EP | 0873759 | 10/1998 |
| GB | 2 130 093 A | 5/1984 |
| GB | 2 209 121 A | 5/1989 |
| JP | 07 178178 | 7/1995 |
| JP | 08 033705 | 2/1996 |
| WO | WO 89/02763 A1 | 4/1989 |
| WO | WO 92/11893 A1 | 7/1992 |
| WO | WO 93/05842 A1 | 4/1993 |
| WO | WO 95/18647 A2 | 7/1995 |
| WO | 2008/021948 | 2/2008 |

OTHER PUBLICATIONS

Quantum—PLEXAR(r) Tie-Layer Resin "Designing PLEXAR Tie-Layer Resigns with Low MVTR Properties," 4 sheets (1989).

Quantum—PLEXAR(r) Tie-Layer Resin "Evaluation of PLEXAR Tie-Layers for EVOH/PET Coextrusion," 2 sheets (1991).

Odian, G., Principles of Polymerization Second Edition, John Wiley & Sons, Table 3, p. 31 (1981).

Brochure: "ASUKA™ 2.9F OTW PTCA Balloon Catheter," Feb. 1994.

Brochure: "Opti-Plast PTA Balloon Dilatation Catheters: for Peripheral Angioplasty," Vas-Cath Incorporated, 4 pages (1991).

Norman G. Gaylord et al., "Compatibilizing Agents: Structure and Function in Polyblends," *J. Macrornol. Sci.-Chem.*, A26(8), pp. 1211-1229 (1989).

Norman G. Gaylord et al., "Maleation of Linear Low-Density Polyethylene Processing," *Journal of Applied Polymer Science*, vol. 44, No. 11, by Reactive Apr. 15, 1992, pp. 1941-1949.

"Physical Constants of Important Polymers," Polymer Handbook,

2nd Edition, A Wiley-Interscience Publication, 1975, p. V-13 thru V-22.
"Physical Constants of Poly(Vinyl Chloride)," Polymer Handbook, 2nd Edition, A Wiley-Interscience Publication, 1975, p. V-41 thru V-50.
"Abrasion & Wear," Encyclopedia of Polymer Science and Engineering, vol. 1, A to Amorphous Polymers, A Wiley-Interscience Publication, 1985, pp. 1-35.
PLEXAR® PX 360 (2 pages).
PLEXAR® PX 209 (2 pages).
Plexar® Tie-Layer Resins, Products, Applications, and Key Properties (3 pages).
Quantum Chemical Corporation Material Safety Data Sheet PLEXAR™ (5 pages).
Chevron Chemical Company Technical Data Sheet Ethylene-Methyl Acrylate Copolymer EMAC SP 2260 (2 pages).
Chevron Chemical Company Technical Data Sheet Ethylene-Methyl Acrylate Copolymer EMAC SP 2205 (2 pages).
Bynel® Coextrudable Adhesive Resins Selector Guide (6 pages).
DuPont Hytrel® Polyester Elastomer Hytrel 7246 (2 pages).
DSM Engineering Plastics Arnitel® —Available Grades List (4 pages).
Petrothene® LS 5060-00 (1 page).
Petrothene® LM 6007-00 (1 page).
Internet printout, "Kynar® PVDF," Www.arkema-inc.com/print.cfm?pag=102, printed. Aug. 9, 2007, 5 sheets.

* cited by examiner

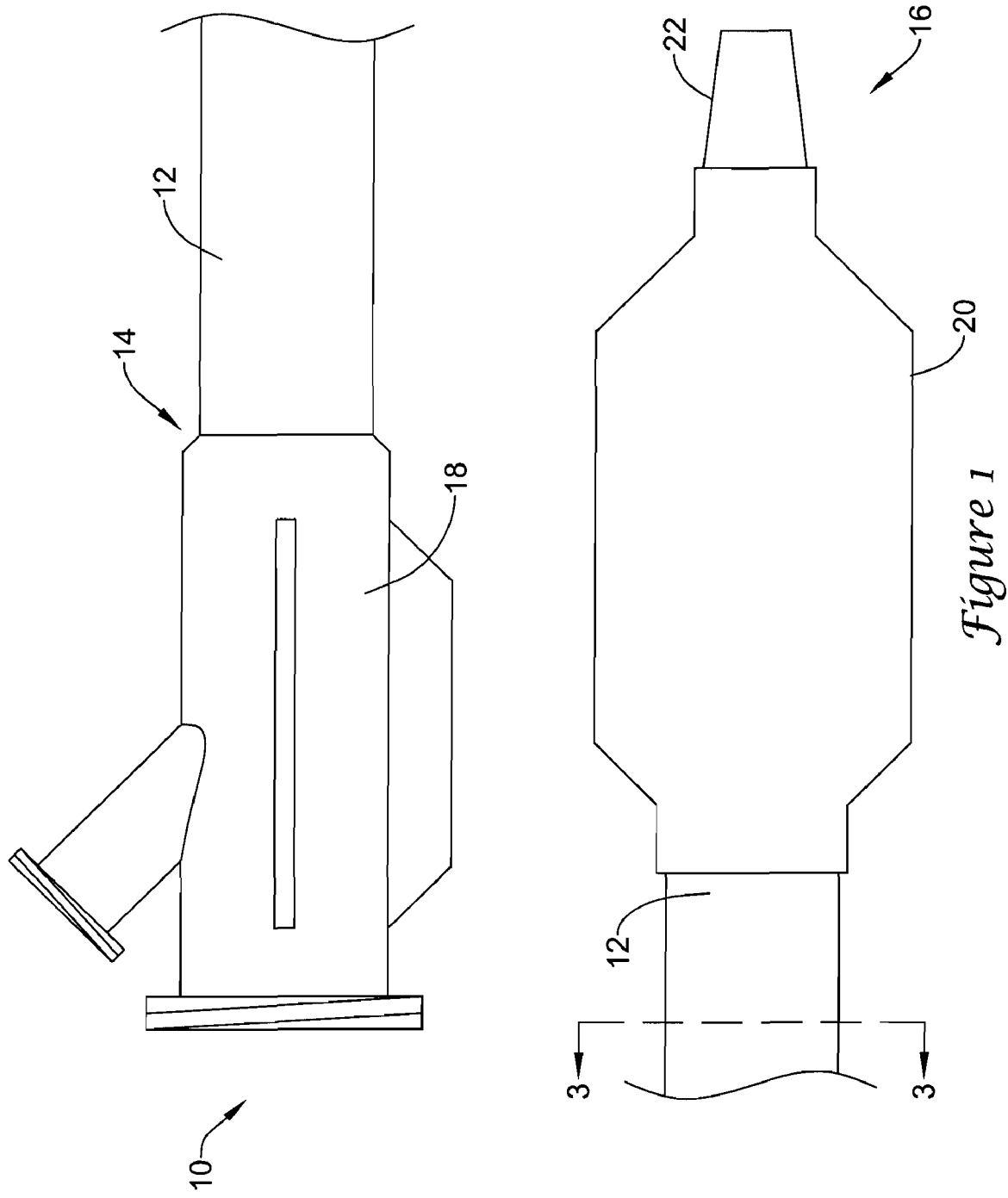

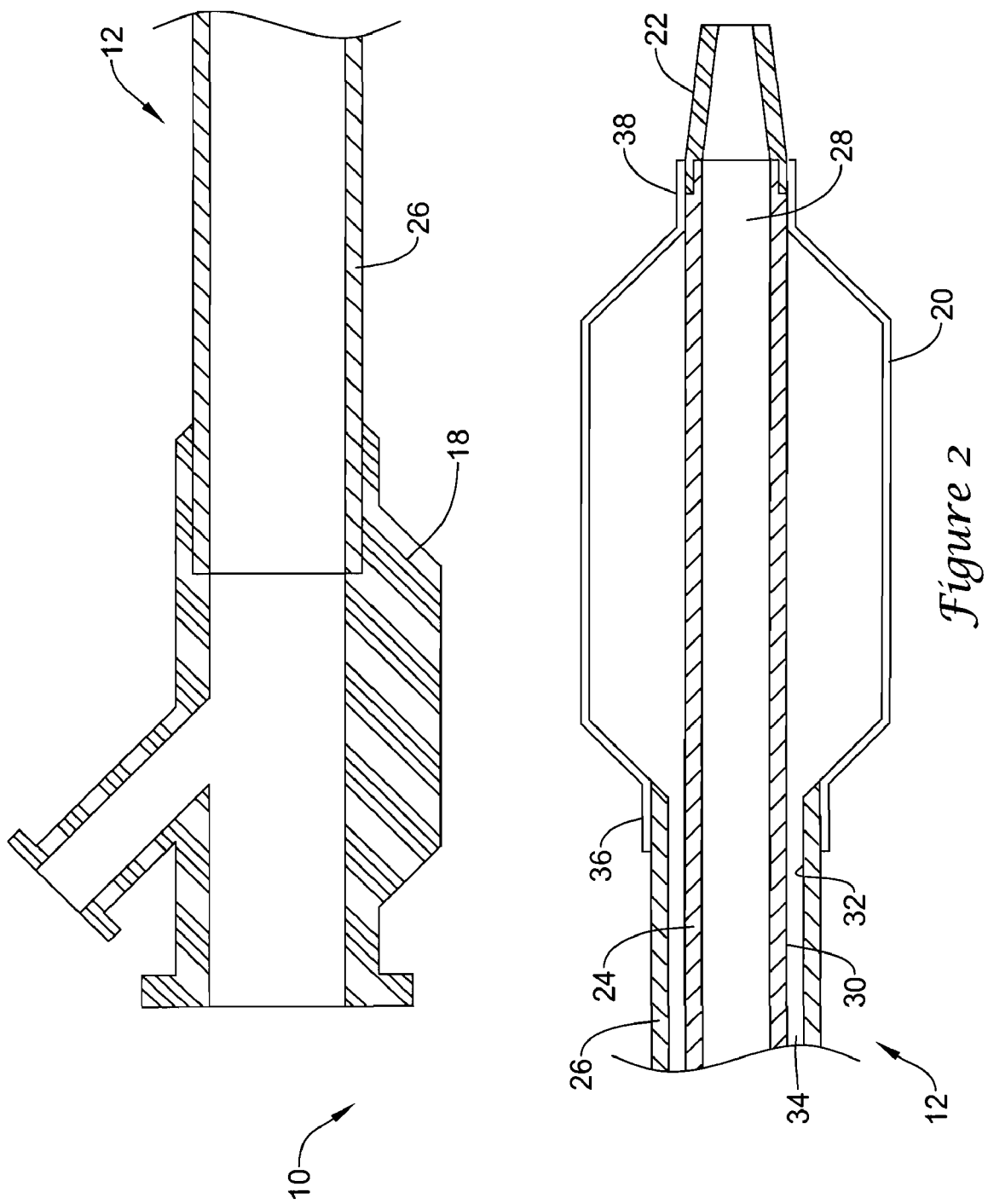

CATHETER HAVING A COEXTRUDED FLUOROPOLYMER LAYER

TECHNICAL FIELD

The invention is directed to elongated medical devices. More particularly, the invention is directed to a catheter shaft having a coextruded fluoropolymer layer directly bonded to another polymer layer.

BACKGROUND

Catheters, such as intravascular catheters, are commonly constructed of multi-layer tubular members including multiple layers of polymeric material. The polymeric material for one layer of the multi-layer tubular member may be chosen for certain desired characteristics, while the polymeric material for another layer of the multi-layer tubular member may be chosen for other certain desired characteristics. In some instances, the polymeric material of the first layer may be incompatible with the polymeric material of the second layer. For example, the polymeric material of the first layer may not be readily bonded or adhered to the polymeric material of the second layer. In such instances, an intermediate layer or tie layer may be placed between the first layer and the second layer. The intermediate or tie layer may readily bond or adhere to each of the first layer and the second layer, thus "tying" the first layer to the second layer.

It is generally known that fluoropolymers, such as polyvinylidene fluoride (PVDF), are generally not bondable to other polymeric materials, such as polyamide, polyether block amide, polyurethane, polyethylene and polyester. Thus, if it is desired to use a fluoropolymer, such as polyvinylidene fluoride (PVDF) as one layer of a multi-layer catheter tubing, and a non-compatible polymer, such as polyamide, polyether block amid, polyurethane, or polyester, as another layer of the multi-layer catheter tubing, then a tie layer is necessary to prevent delamination of the fluoropolymer layer from the other polymer layer.

The inclusion of the intermediate or tie layer in the catheter tubing adds thickness to the tubing, as well as adds additional cost to the manufacture of the catheter tubing. For instance, in addition to the additional cost of the tie layer material, an additional extruder would be necessary in order to co-extrude the tie layer with the inner and outer layers of the tubular member.

It would be advantageous to manufacture a catheter tube having a fluoropolymer layer, such as polyvinylidene fluoride (PVDF), directly bonded to another polymer layer without the need for an intervening tie layer disposed between the fluoropolymer layer and the other polymer layer. Thus, such catheter tubing may benefit from the inclusion of a fluoropolymer layer without the concern of the fluoropolymer layer delaminating from the other polymeric layer of the catheter tube.

SUMMARY

The disclosure is directed to several alternative designs, materials and methods of manufacturing medical device structures and assemblies.

Accordingly, one illustrative embodiment is a catheter shaft including an elongate tubular member having a first end, a second end and a tubular wall extending between the first end and the second end. The elongate tubular member includes an outer polymeric layer formed of a polymer generally not bondable to fluoropolymers, and an inner fluoropolymer layer directly bonded to the outer polymeric layer. The inner fluoropolymer layer includes a functionalized polyvinylidene fluoride which has a bonding affinity to the outer polymeric layer, wherein the functionalized polyvinylidene fluoride includes reactive functional groups chemically bonded to a polymer chain of a polyvinylidene fluoride.

Another illustrative embodiment is a catheter shaft including an elongate tubular member having a first end, a second end and a tubular wall extending between the first end and the second end. The elongate tubular member includes an inner polymeric layer formed of a polymer generally not bondable to fluoropolymers, and an outer fluoropolymer layer directly bonded to the inner polymeric layer. The outer fluoropolymer layer includes a functionalized polyvinylidene fluoride which has a bonding affinity to the inner polymeric layer, wherein the functionalized polyvinylidene fluoride includes reactive functional groups chemically bonded to a polymer chain of a polyvinylidene fluoride.

Another illustrative embodiment is a method of forming a catheter shaft. The method includes extruding a first polymer in a molten state onto a mandrel, forming a first molten layer of the first polymer. A second polymer is extruded in a molten state over the first molten layer of the first polymer, forming a second molten layer of the second polymer over the first molten layer of the first polymer. The first molten layer of the first polymer and the second molten layer of the second polymer are then passed through an extrusion die while the first molten layer and the second molten layer remain in their molten state. Then the first molten layer of the first polymer and the second molten layer of the second polymer are allowed to cool, wherein a bilayer polymer tube is formed having an outer layer formed of the first polymer directly bonded to an inner layer formed of the second polymer without any intervening layer positioned between the inner layer and the outer layer of the bilayer polymeric tube. One of the first polymer and the second polymer is a functionalized polyvinylidene fluoride, while the other of the first polymer and the second polymer is a polymer generally not compatible with polyvinylidene fluoride.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 1 is a plan view of an illustrative catheter;

FIG. 2 is a longitudinal cross-sectional view of the catheter of FIG. 1;

Figure 4:
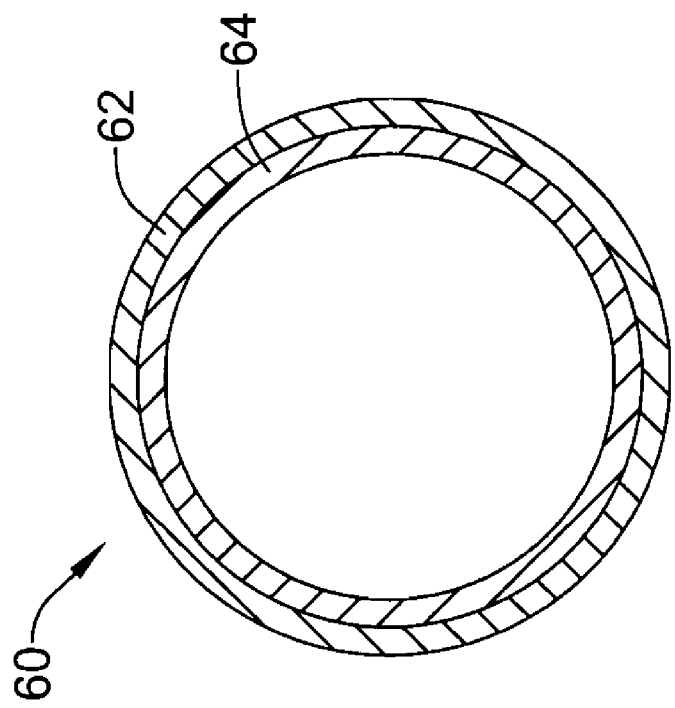
FIG. 4 is a cross-sectional view on a tubular member of another medical device.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

A catheter 10, generally disclosed as an angioplasty catheter, is illustrated in FIG. 1. Although the catheter 10 is described as an angioplasty catheter, one of skill in the art would understand that the present discussion may apply equally to other types of catheters, such as guide catheters, stent delivery catheters, biliary catheters, urethra catheters, atherectomy catheters, and other medical catheters, as well as guidewires, and the like.

The catheter 10 may include an elongate shaft 12 extending from a proximal end 14 to a distal end 16. A hub assembly 18 may be attached to the proximal end 14 of the elongate shaft 12. Additionally, the catheter 10 may include an inflatable balloon 20 disposed on a distal region of the elongate shaft 12. A distal tip 22, such as an atraumatic tip, may extend distal of the balloon 20 at the distal end 16 of the elongate shaft 12.

FIG. 2 is a cross-sectional view of the catheter 10 of FIG. 1. As shown in FIG. 2, the shaft 12 may include an inner tubular member 24 and an outer tubular member 26. The inner tubular member 24 may include a guidewire lumen 28 extending therethrough for receiving a guidewire. The proximal end of the outer tubular member 26 may be disposed in the hub assembly 18 and secured thereto.

The inner tubular member 24 may be disposed within the outer tubular member 26 such that the outer surface 30 of the inner tubular member 24 is spaced away from the inner surface 32 of the outer tubular member, defining an inflation lumen 34 between the inner tubular member 24 and the outer tubular member 26. The inflation lumen 34 may be in fluid communication with the interior of the balloon 20, such that an inflation fluid may be directed through the inflation lumen 34 to the interior of the balloon 20 in order to inflate the balloon 20 during a medical procedure.

As shown in FIG. 2, the balloon 20 may have a proximal waist 36 and a distal waist 38. The distal waist 38 of the balloon 20 may be secured to the distal end of the inner tubular member 24, and the proximal waist 36 of the balloon 20 may be secured to the distal end of the outer tubular member 26. The balloon 20 may be secured to the inner tubular member 24 and the outer tubular member 26 by adhesive bonding, laser welding, or the like.

Figure 3:
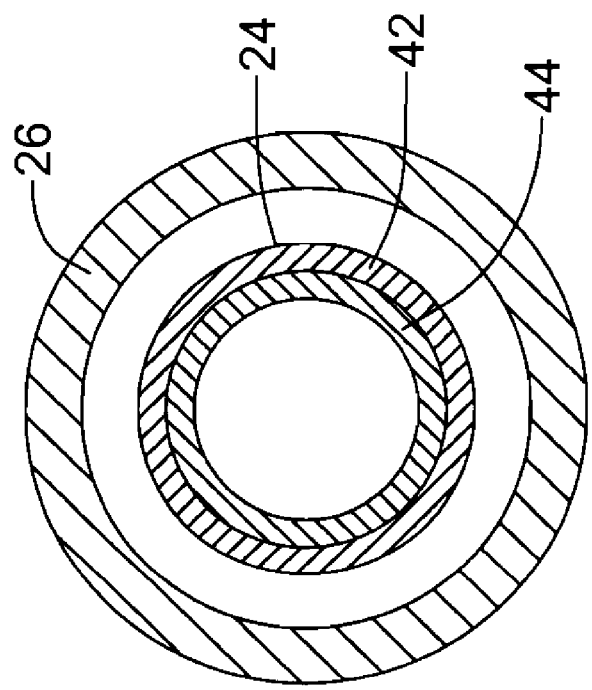
FIG. 3 is a transverse cross-sectional view of the shaft of the catheter of FIG. 1 taken along line 3-3.

FIG. 3 is a cross-section of the catheter shaft 12 transverse to the longitudinal axis of the catheter shaft 12. As shown in FIG. 3, the inner tubular member 24 may be a multi-layer tubular member, such as a bilayer tubular member having an outer layer 42 and an inner layer 44. The inner layer 44 may be directly bonded to the outer layer 42 of the inner tubular member 24, with no intervening layer between the inner layer 44 and the outer layer 42.

The outer layer 42 may be formed of a polymeric material, such as polyamide, polyether block amide, polyurethane, polyethylene or polyether. The inner layer 44 of the inner tubular member 24 may be a fluoropolymer, such as polyvinylidene fluoride (PVDF), giving the inner layer 44 lubricious properties. Namely, the inner layer 44 may be formed of a functionalized polyvinylidene fluoride which is directly bonded to the outer layer 42. Directly bonded or adhered is meant that there is no intervening tie layer present. It is the affinity of the functionalized polyvinylidene fluoride inner layer 44 that causes the bonding or adhesion of the layers 42/44 without the use of a tie layer between the inner and outer layers 44/42. Thus, unlike other polyvinylidene fluoride polymers which are not readily bonded to other polymeric materials, the functionalized polyvinylidene fluoride inner layer 44 may be directly bonded, such as covalently bonded, to the polymer outer layer 42.

The functionalized polyvinylidene fluoride includes reactive functional groups chemically bonded to a polymer chain of polyvinylidene fluoride. For example, the functionalized polyvinylidene fluoride may be KYNAR® ADX, sold by Arkema, Inc. of Philadelphia, Pa. The reactive functional groups of the functionalized polyvinylidene fluoride layer may form covalent bonds with the polymer chain of the outer layer 42.

In some embodiments, the reactive functional groups include an unsaturated carboxylic acid, such as maleic acid, fumaric acid, cinnamic acid, crotonic acid, or linoleic acid. In some embodiments, the reactive functional groups may include maleic anhydride.

In some embodiments, the functionalized polyvinylidene fluoride may include radiation-grafted reactive functional groups. The radiation-grafted functional groups may include a compound including a carboxylic acid, or a derivative of a carboxylic acid.

FIG. 4 is a cross-section of another tubular member 60 which may be used in a medical device, such as a catheter. The tubular member 60 may be a bilayer tubular member having an outer layer 62 and an inner layer 64. The inner layer 64 may be directly bonded to the outer layer 62 of the tubular member 60, with no intervening layer between the inner layer 64 and the outer layer 62.

The inner layer 64 may be formed of a polymeric material, such as polyamide, polyether block amide, polyurethane, polyethylene or polyether. The outer layer 62 of the tubular member 60 may be a fluoropolymer, such as polyvinylidene fluoride (PVDF), giving the outer layer 62 lubricious properties. Namely, the outer layer 62 may be formed of a functionalized polyvinylidene fluoride which is directly bonded to the inner layer 64. Directly bonded or adhered is meant that there is no intervening tie layer present. It is the affinity of the functionalized polyvinylidene fluoride outer layer 62 that causes the bonding or adhesion of the layers 62/64 without the use of a tie layer between the inner and outer layers 64/62. Thus, unlike other polyvinylidene fluoride polymers which are not readily bonded to other polymeric materials, the functionalized polyvinylidene fluoride outer layer 62 may be directly bonded, such as covalently bonded, to the polymer inner layer 64.

The functionalized polyvinylidene fluoride includes reactive functional groups chemically bonded to a polymer chain of polyvinylidene fluoride. For example, the functionalized polyvinylidene fluoride may be KYNAR® ADX, sold by Arkema, Inc. of Philadelphia, Pa. The reactive functional groups of the functionalized polyvinylidene fluoride layer may form covalent bonds with the polymer chain of the inner layer 64.

In some embodiments, the reactive functional groups include an unsaturated carboxylic acid, such as maleic acid, fumaric acid, cinnamic acid, crotonic acid, or linoleic acid. In some embodiments, the reactive functional groups may include maleic anhydride.

In some embodiments, the functionalized polyvinylidene fluoride may include radiation-grafted reactive functional groups. The radiation-grafted functional groups may include a compound including a carboxylic acid, or a derivative of a carboxylic acid.

Either the tubular member 24 shown in FIG. 3 or the tubular member 60 shown in FIG. 4 may be formed in a coextrusion process where the outer layer 42/62 is coextruded simultaneously with the inner layer 44/64. In describing the outer layer 42/62 as being coextruded simultaneously with the inner layer 44/64, what is meant is that the outer layer 42/62 is coextruded with the inner layer 44/64 during the same extrusion process where both the inner layer 44/64 and the outer layer 42/62 are concurrently in the molten state of the polymer during the extrusion process. By coextruding the outer layer 42/62 over the inner layer 44/64, the layers 44/64 may be directly bonded to one another. For instance, the inclusion of the reactive functional groups chemically bonded to a polymer chain of polyvinylidene fluoride of the functionalized polyvinylidene fluoride may form a chemical bond, such as a covalent bond, between the outer layer 42/62 and the inner layer 44/64 of the tubular member 24/60.

Figure 5:
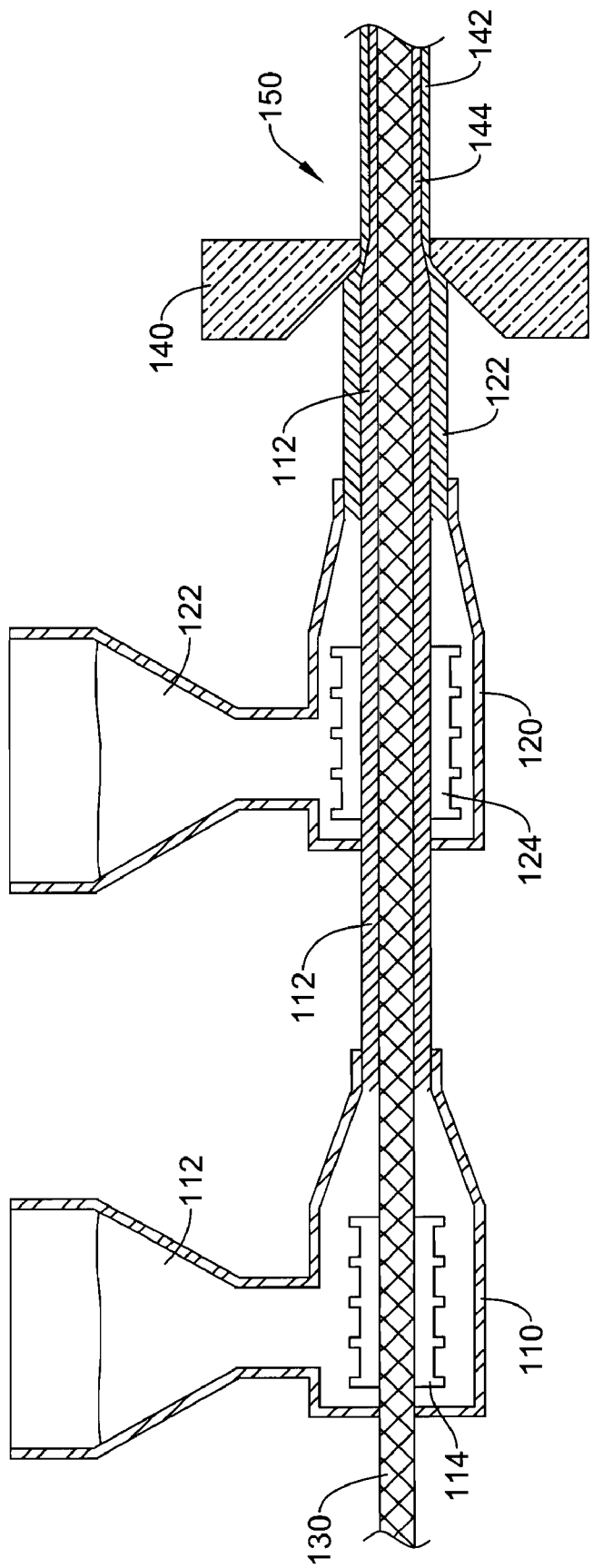
FIG. 5 is a cross-sectional view of an extrusion system for co-extruding a multi-layer tubular member.

As shown in FIG. 5, an illustrative extrusion system which may be used during the coextrusion process may include a first extruder 110, a second extruder 120, a mandrel 130, and an extrusion die 140.

A first molten polymer 112 may be extruded onto the mandrel 130 by the first extruder 110. For instance, the screw 114 of the first extruder 110 may feed the first molten polymer 112 out the head of the extruder 110 over the mandrel 130. The mandrel 130, coated with the first molten polymer 112 may then enter the second extruder 120. A second molten polymer 122 may be extruded over the first molten polymer 112 by the second extruder 120. For instance, the screw 124 of the second extruder 120 may feed the second molten polymer 122 out the head of the extruder 120 over the first molten polymer 112. Thus, a layer of the first molten polymer 112 and a layer of the second molten polymer 122 may be coaxially disposed over the mandrel 130.

The layer of the first molten polymer 112, the layer of the second molten polymer 122, and the mandrel 130 may then be passed through the extrusion die 140 while the first layer of molten polymer 112 and the second layer of molten polymer 122 remain in their molten state. As the layers of molten polymer are passed through the extrusion die 140, a bilayer polymer tube 150 is formed having an outer layer 142 directly bonded to an inner layer 144, without any intervening layer positioned between the inner layer 144 and the outer layer 142.

One of the inner layer 144 and the outer layer 142 may be a functionalized polyvinylidene fluoropolymer, while the other of the inner layer 144 and the outer layer 142 may be a polymer generally not compatible with fluoropolymers, such as polyvinylidene fluoropolymer. For example, the other of the inner layer 144 and the outer layer 142 may be polyamide, polyether block amide, polyurethane, polyethylene or polyether.

When a functionalized polyvinylidene fluoropolymer as described herein is used as one of the inner layer 144 or the outer layer 142, the inner layer 144 may be chemically bonded to the outer layer 142 due to the inclusion of the reactive functional groups chemically bonded to a polymer chain of polyvinylidene fluoride of the functionalized polyvinylidene fluoride.

The bilayer polymer tube 150 may be used as a tubular member of a medical device, for example an inner tubular member or outer tubular member of a catheter shaft. The chemical bonds formed between the inner layer 144 and the outer layer 142 may prevent delamination of the polymer tube 150 during use. Thus, it can be seen that a tubular member of a catheter including a fluoropolymer layer giving the tubular member lubricious properties may be manufactured in which the lubricious fluoropolymer layer is directly bonded to another polymeric layer generally not bondable to a fluoropolymer.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A catheter shaft comprising:
   an elongate tubular member having a first end, a second end and a tubular wall extending between the first end and the second end;
   the elongate tubular member including:
      i) an outer polymeric layer formed of a polymer generally not bondable to fluoropolymers; and
      ii) an inner fluoropolymer layer directly bonded to the outer polymeric layer;
      wherein the inner fluoropolymer layer includes a functionalized polyvinylidene fluoride which has a bonding affinity to the outer polymeric layer;
      wherein the functionalized polyvinylidene fluoride includes reactive functional groups chemically bonded to a polymer chain of a polyvinylidene fluoride.

2. The catheter shaft of claim 1, wherein the reactive functional groups include maleic anhydride.

3. The catheter shaft of claim 1, wherein the functionalized polyvinylidene fluoride includes radiation-grafted reactive functional groups.

4. The catheter shaft of claim 3, wherein the radiation-grafted reactive functional groups include a compound including a carboxylic acid or a derivative of a carboxylic acid.

5. The catheter shaft of claim 3, wherein the radiation-grafted reactive functional groups include maleic anhydride.

6. The catheter shaft of claim 1, wherein the functionalized polyvinylidene fluoride is covalently bonded to the polymer of the outer polymeric layer.

7. The catheter shaft of claim 1, wherein the outer polymeric layer is a polyether block amide layer.

8. The catheter shaft of claim 1, wherein the outer polymeric layer is a polyester layer.

9. The catheter shaft of claim 1, wherein the outer polymeric layer is a polyurethane layer.

10. The catheter shaft of claim 1, wherein the outer polymeric layer is a polyethylene layer.

11. A catheter shaft comprising:
   an elongate tubular member having a first end, a second end and a tubular wall extending between the first end and the second end;
   the elongate tubular member including:
      i) an inner polymeric layer formed of a polymer generally not bondable to fluoropolymers; and
      ii) an outer fluoropolymer layer directly bonded to the inner polymeric layer;
      wherein the outer fluoropolymer layer includes a functionalized polyvinylidene fluoride which has a bonding affinity to the inner polymeric layer;
      wherein the functionalized polyvinylidene fluoride includes reactive functional groups chemically bonded to a polymer chain of a polyvinylidene fluoride.

12. The catheter shaft of claim 11, wherein the reactive functional groups include maleic anhydride.

13. The catheter shaft of claim 11, wherein the functionalized polyvinylidene fluoride includes radiation-grafted reactive functional groups.

14. The catheter shaft of claim 13, wherein the radiation-grafted reactive functional groups include a compound including a carboxylic acid or a derivative of a carboxylic acid.

15. The catheter shaft of claim 13, wherein the radiation-grafted reactive functional groups include maleic anhydride.

16. The catheter shaft of claim 11, wherein the functionalized polyvinylidene fluoride is covalently bonded to the polymer of the outer polymeric layer.

17. The catheter shaft of claim 11, wherein the inner polymeric layer is a polyether block amide layer.

18. The catheter shaft of claim 11, wherein the inner polymeric layer is a polyester layer.

19. The catheter shaft of claim 11, wherein the inner polymeric layer is a polyurethane layer.

20. The catheter shaft of claim 11, wherein the inner polymeric layer is a polyethylene layer.

21. A catheter shaft comprising:
   an elongate tubular member having a proximal end, a distal end and a tubular wall extending between the first end and the second end;
   a hub assembly attached to the proximal end of the elongate tubular member;
   an inflatable balloon disposed adjacent the distal end of the elongate tubular member;
   the elongate tubular member including:
      i) an outer polymeric layer formed of a polymer generally not bondable to fluoropolymers; and
      ii) an inner fluoropolymer layer directly bonded to the outer polymeric layer;
      wherein the inner fluoropolymer layer includes a functionalized polyvinylidene fluoride which has a bonding affinity to the outer polymeric layer;
   wherein the functionalized polyvinylidene fluoride includes reactive functional groups chemically bonded to a polymer chain of a polyvinylidene fluoride.

22. The catheter shaft of claim 1, wherein the reactive functional groups include maleic anhydride.

23. The catheter shaft of claim 1, wherein the functionalized polyvinylidene fluoride includes radiation-grafted reactive functional groups.

24. The catheter shaft of claim 23, wherein the radiation-grafted reactive functional groups include a compound including a carboxylic acid or a derivative of a carboxylic acid.

25. The catheter shaft of claim 23, wherein the radiation-grafted reactive functional groups include maleic anhydride.

26. The catheter shaft of claim 1, wherein the functionalized polyvinylidene fluoride is covalently bonded to the polymer of the outer polymeric layer.

* * * * *